United States Patent [19]
Johnson et al.

[11] Patent Number: 5,363,708
[45] Date of Patent: Nov. 15, 1994

[54] SELF-CLEARING MATERIAL SENSING APPARATUS

[75] Inventors: David M. Johnson, Anoka; Larry C. McNeff, Hopkins, both of Minn.

[73] Assignee: SarTec Corporation, Anoka, Minn.

[21] Appl. No.: 974,199

[22] Filed: Nov. 10, 1992

[51] Int. Cl.5 .......................................... G01M 19/00
[52] U.S. Cl. ..................................... 73/865.8; 73/73; 73/866
[58] Field of Search .................... 73/866, 865.8, 73

[56] References Cited

U.S. PATENT DOCUMENTS 4,590,795  5/1986  Oetiker et al. ........................ 73/73
5,125,275  6/1992  Anthony et al. ..................... 73/866

Primary Examiner—Richard E. Chilcot, Jr.
Assistant Examiner—Joseph L. Felber
Attorney, Agent, or Firm—Merchant, Gould, Smith, Edell, Welter & Schmidt

[57] ABSTRACT

A self-clearing material sensing apparatus is provided for sensing a physical parameter of a particulate material flowing through a conduit. The self-clearing material sensing apparatus includes a sensor device and funnel for directing a consistent flow of the particulate material to an area proximate the sensor device. The funnel has a read configuration and a clearance configuration and includes an upper inlet and a lower outlet including a narrowing below the upper inlet when the funnel is in the read configuration. The narrowing is adjustable for increasing the cross-sectional area of the narrowing when the funnel is changed from the read configuration to the clearance configuration. An actuation mechanism is provided for changing the funnel from the read configuration to the clearance configuration, and from the clearance configuration back to the read configuration, to periodically release any material clogged within the funnel. A scalper grate having clearing blades is disposed above the funnel inlet to prevent larger foreign objects from entering the funnel.

10 Claims, 5 Drawing Sheets 5,363,708

SELF-CLEARING MATERIAL SENSING APPARATUS

FIELD OF THE INVENTION

This invention pertains to sensor devices for sensing a physical parameter of a particulate material. More particularly, the invention concerns a device for sensing the moisture content of a grain flow.

BACKGROUND OF THE INVENTION

In a grain processing environment, it is often useful to store grain with a low moisture content. When the stored grain is ready to be processed, aqueous moisturizing agents are often added to the grain prior to processing to increase the moisture content of the grain. When the grain is being transferred from a storage area to a processing area, it has proven helpful to install a moisture sensor to continuously monitor the moisture content of the grain flow. Based on the readings from the moisture sensor, an appropriate amount of water is added to the grain to maintain a desired moisture content of the grain to be processed.

In utilizing these moisture sensors, it is necessary to maintain a consistent, compact flow of grain around the sensor to provide an accurate reading. Accordingly, it is known in the art to provide a funnel surrounding the sensor to ensure a steady flow of grain. A problem, however, with the use of a funnel concerns the potential clogging of the funnel either by the grain itself or by some larger foreign objects, such as cornstalks. The clogging of the funnel is even more of a problem when the funnel and sensor are placed downstream in the flow of grain from the moisture addition area.

It is important to note that when the funnel is clogged, the sensor only reads the moisture content of the grain lodged in the funnel and thus inaccurately monitors the grain which continues to flow around the funnel. Previously, when the funnel clogged, it was necessary to manually unclog the funnel. This often entailed sending a person inside the grain flow area to manually unclog the funnel. Accordingly, a self-clearing funnel is needed to automatically unclog the funnel and to prevent larger foreign objects (i.e., cornstalks, corn cobs, corn husks and other refuse collected with grain during harvesting) from entering the funnel.

It will be appreciated from the foregoing that prior art devices present problems which are in need of solutions. The present invention provides solutions for these and other problems.

SUMMARY OF THE INVENTION

In the preferred embodiment, a self-clearing material sensing apparatus is disclosed for sensing a physical parameter of a particulate material. The material sensing apparatus includes a sensor device and funnel means for directing a consistent flow of the particulate material to an area proximate the sensor device. The funnel means has a read configuration and a clearance configuration and includes an upper inlet and a lower outlet. When the funnel means is in the read configuration, the lower outlet includes a narrowing below the upper inlet. The cross-sectional area of the upper inlet is greater than the cross-sectional area of the narrowing when the material sensing apparatus is in the read configuration.

In a preferred embodiment, the funnel means further include narrowing adjustment means which include a pivotal connection and an extender arm. The preferred funnel means include a tapered member which is pivotally connected to a vertical plate. When the extender arm is extended, a lower portion of the tapered member pivots away from the vertical plate to increase the cross-sectional area of the narrowing when the funnel is changed from the read configuration to the clearance configuration in order to release any material clogged in the funnel. Actuation means are preferably provided which include an actuating cylinder which is connected to the extender arm to change the funnel from the read configuration to the clearance configuration and from the clearance configuration back to the read configuration.

Preferably, a scalper grate is disposed above the upper inlet of the funnel to prevent larger foreign objects from entering the funnel. Scalper clearing blades connected to a further actuating cylinder are included for periodic insertion between the grate members to clear the scalper grate.

The above described features and advantages along with various other advantages and features of novelty are pointed out with particularity in the claims of the present application which form a part hereof. However, for a better understanding of the invention, its advantages, and objects attained by its use, reference should be made to the drawings which form a further part of the present application and to the accompanying descriptive matter in which there is illustrated and described preferred embodiments of the invention.

DETAILED DESCRIPTION OF THE PREFERRED EMBODIMENTS

Figure 1:
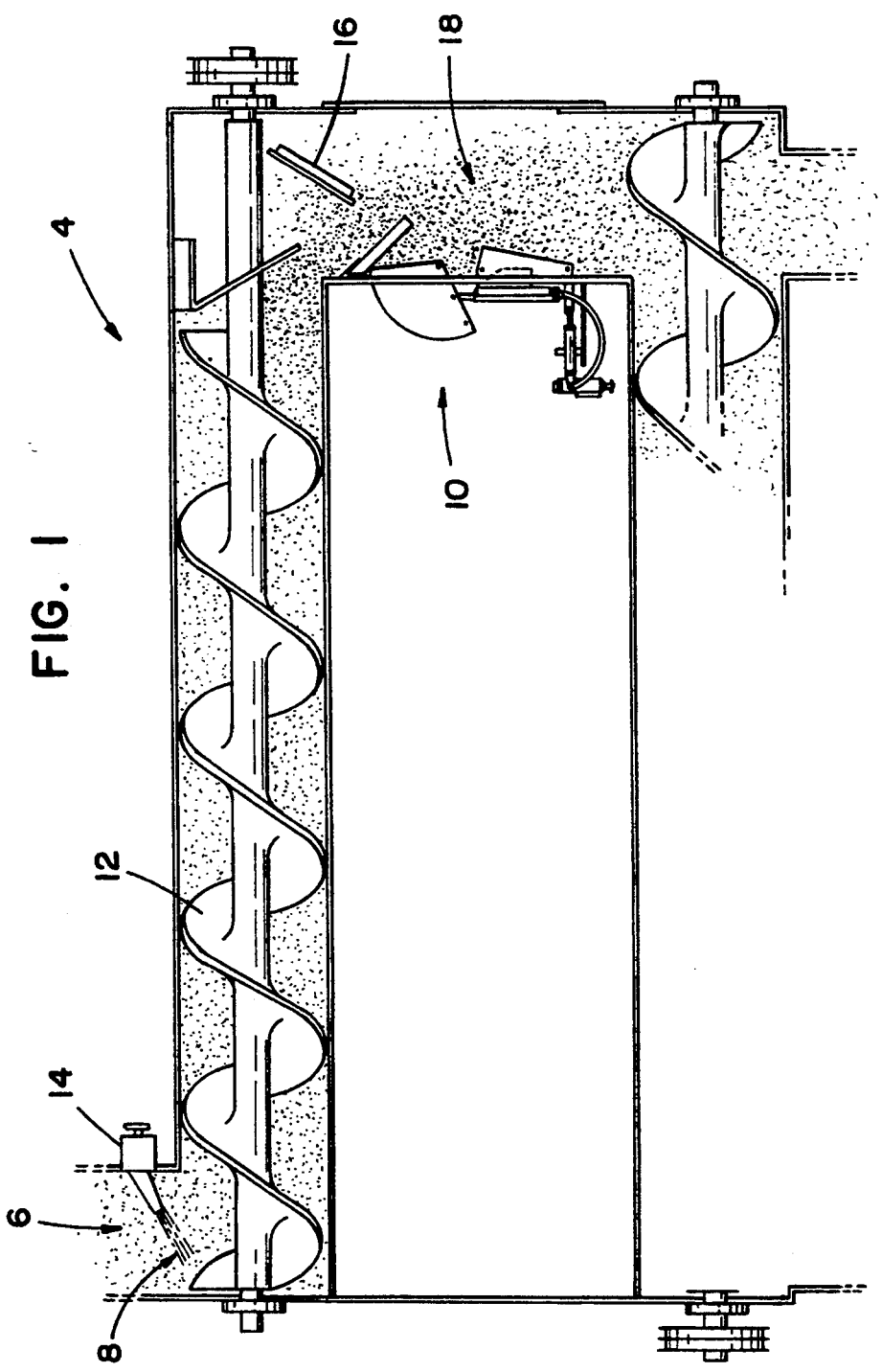
FIG. 1 is a side elevation view of a preferred self-clearing material sensing apparatus within a grain transferring environment.

Referring now to the drawings, in which similar elements are numbered identically throughout, a description of a preferred embodiment of the present invention is provided. In FIG. 1, a preferred self-clearing material sensing apparatus 10 is shown positioned within a grain transfer system 4. As the grain 6 is transferred by augers 12 from a grain storage area (not shown) to a grain processing area (not shown), the grain flow is directed into the self-clearing material sensing apparatus 10 which senses a physical parameter of the particulate grain. In the preferred embodiment shown in FIG. 1, the material sensing apparatus 10 monitors the moisture content of the grain 6 to provide a continuous reading for the grain being transferred. Based on the reading from the material sensing apparatus 10, moisture 8, often in the form of water, but more preferably in the form of an aqueous solution including a surfactant, such as an aqueous yucca extract, is added to the grain 6 by a spray applicator 14 upstream from the self-clearing material sensing apparatus 10 to maintain a consistent moisture content for the grain flow. The self-clearing material sensing apparatus 10 is preferably disposed in a vertical section of the grain transfer system 4 where a sample of the grain can easily be directed, with the use of a guide portion 16, and under the force of gravity into the material sensing apparatus 10.

Figure 2:
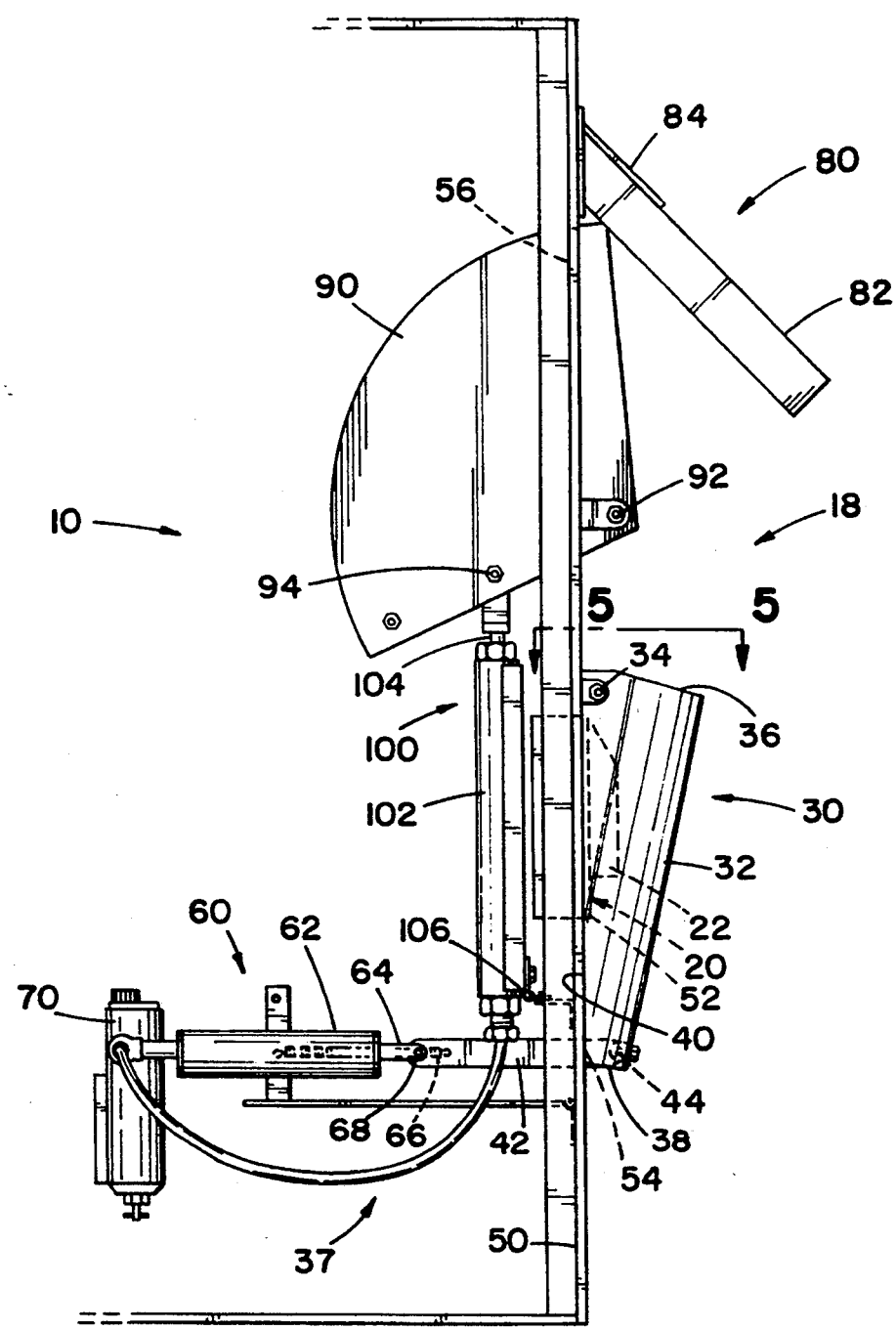
FIG. 2 is a side elevation view of the self-clearing material sensing apparatus shown in FIG. 1 in the read configuration.

With further reference to FIG. 2, the preferred self-clearing material sensing apparatus 10 includes a sensor device 20 which is disposed within a slot 52 in a vertical plate 50 so that the sensing portion 22 of the device extends into the interior of the grain flow conduit 18. In the preferred embodiment, this sensor device 20 is a moisture sensor designed to measure the moisture content of the grain passing by the sensor. Although such moisture sensors are well known in the art, typical moisture sensor which can be used is a Calcu-Dry TM moisture monitor manufactured by DMC Corporation. It will be appreciated that the sensor includes control means (not shown) to relay the signal received by the sensor to an appropriate controller which adjusts the amount of moisture being added (at 14) to the grain based on the sensor readings. In this way, the moisture content of the grain is maintained at a generally uniform level. Any of the known moisture sensors which supply the necessary functions can be used in the present invention.

In order for the sensor device 20 to accurately measure the moisture content of the grain being transferred, it is necessary to provide a compact, uniform flow of grain around the sensor. In conjunction with this purpose, the self-clearing material sensing apparatus 10 includes a funnel 30 which surrounds the sensor device to direct a uniform flow of grain 6 to an area proximate the sensor device 20. The funnel 30 is formed by a tapered member 32 which is secured by funnel pivot connections 34 to the vertical plate 50. The funnel 30 has an upper inlet 36 having a first cross-sectional area and a lower outlet 38 having a second cross-sectional area. When the funnel is in the read configuration, as shown in FIG. 2, the first cross-sectional area of the inlet 36 is greater than the second cross-sectional area of the lower outlet 38. In this read configuration, the longitudinal side edges 40 of the tapered member 32 are disposed against the vertical plate 50. It is noted that when the self-clearing material sensing apparatus 10 is in the read configuration, the funnel 30 directs a compact, uniform flow of grain to an area proximate the sensing portion 22 of the sensor or sensor device 20 so that the sensor 20 can accurately measure the moisture content of the grain flow.

Pursuant to another feature of this invention, the funnel 30 includes an adjustment mechanism 37 for adjusting the second cross-sectional area of the lower outlet 38. This mechanism is useful because the funnel 30 may occasionally become clogged with grain. When the funnel 30 is clogged, the grain continues to flow outside the funnel. The sensor 20, however, only measures the moisture content of the grain clogged in the funnel 30 and consequently does not provide an accurate reading of the moisture content of the continuing grain flow.

Figure 3:
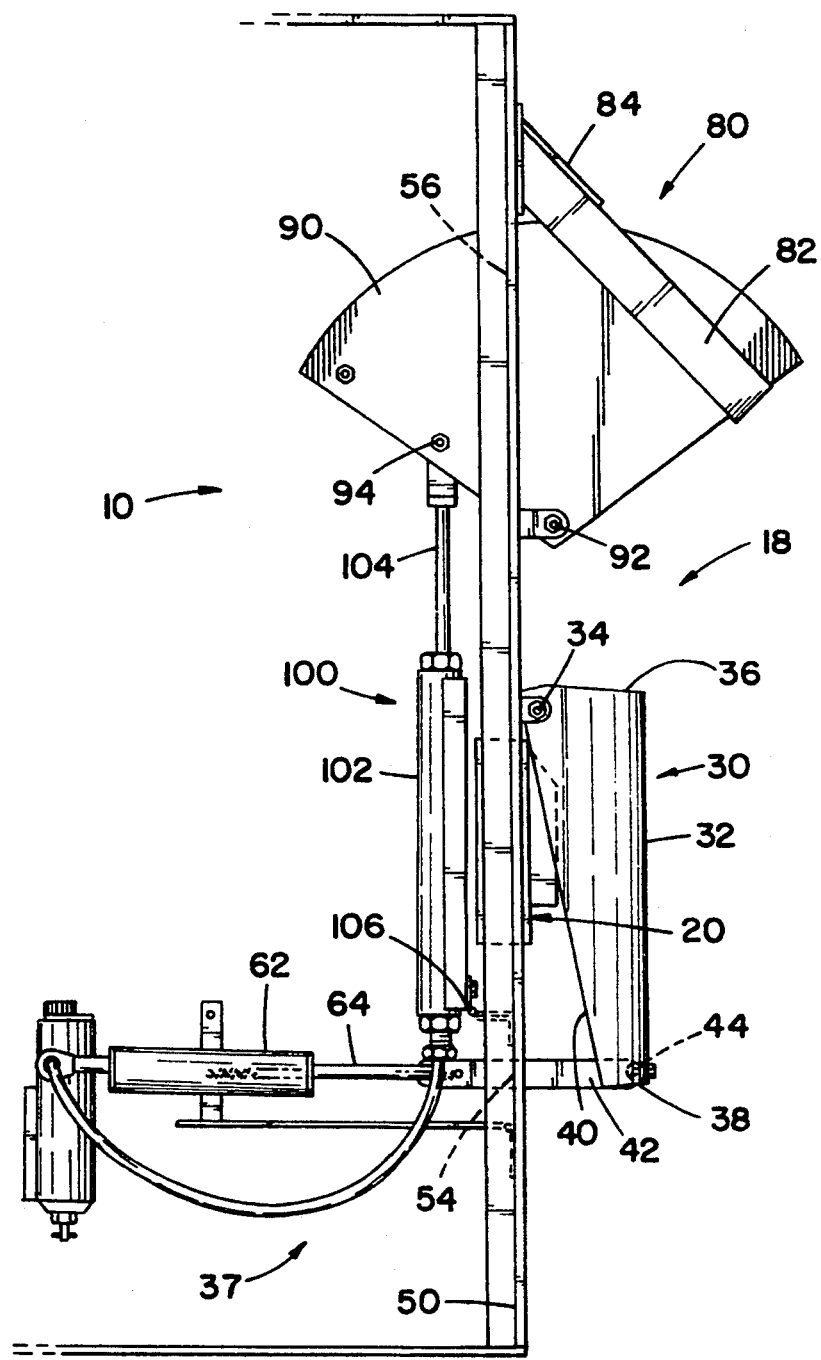
FIG. 3 is a side elevation view of the self-clearing material sensing apparatus shown in FIG. 1 in the clearance configuration.
Figure 5:
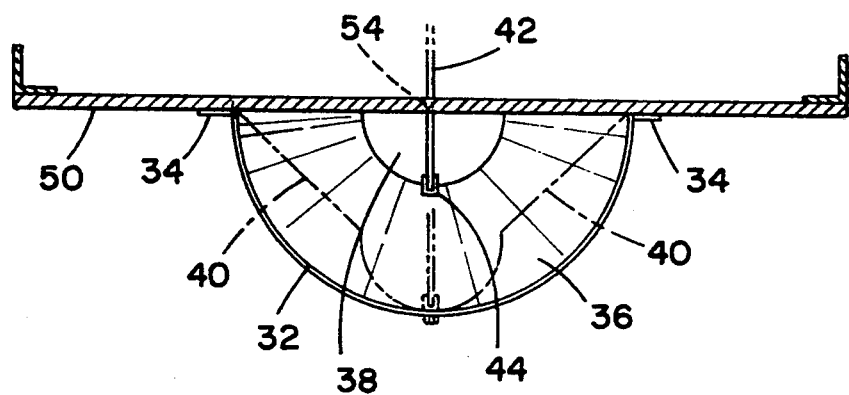
FIG. 5 is a view taken along line 5—5 in FIG. 2.

The adjustment mechanism 37 of the material sensing apparatus 10 includes an extender arm 42 which is disposed in a slot 54 in the vertical plate 50 and is secured through a pivotal connection 44 to the lower outlet 38 of the funnel. As shown in FIG. 3, the self-clearing material sensing apparatus 10 is movable to a clearance configuration in which the cross-sectional area of the outlet 38 is increased to efficiently release any grain which is clogged in the funnel 30. The material sensing apparatus 10 is changeable from the read configuration, shown in FIG. 2, to the clearance configuration, shown in FIG. 3, by the movement of the extender arm 42 through the vertical plate 50 and toward the interior of the grain flow area 18. This movement of the extender arm 42 serves to rotate the tapered member 32 about the funnel pivot connections 34 such that the side edges 40 of the tapered member 32 are positioned away from the vertical plate 50. In this clearance configuration, the cross-sectional area of the lower outlet 38 is substantially increased to allow any grain clogged within the funnel to be released. As illustrated in phantom in FIG. 5, the side edges 40 and lower outlet 38 of the tapered member 32 are positioned away from the vertical plate 50 when in a clearance configuration (for clarity purposes, the sensor device 20 is not shown in FIG. 5).

Figure 6:
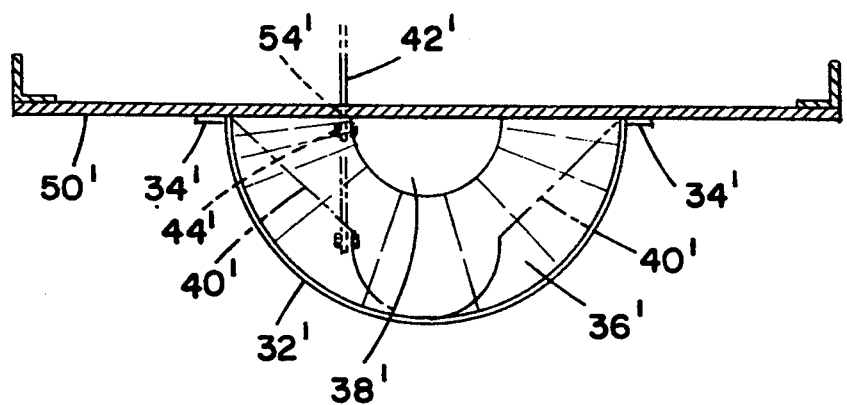
FIG. 6 is a view of an alternative embodiment similar to the view of FIG. 5.

In a preferred embodiment of the present invention as shown in FIG. 6, the extender arm 42' is secured to the lower outlet 38' adjacent a side edge 40' of the tapered member 32' through a pivot connection 44'. It will be appreciated that by disposing pivot connection 44' adjacent a side edge 40' of the outlet 38', the extender arm 42' is positioned generally peripheral to the grain flow through the outlet 38' when the material sensing apparatus 10' (not shown) is in the read configuration. Thus, this positioning of the extender arm 42' allows for efficient grain flow through the funnel outlet 38'.

In connection with another feature of this invention, an actuating mechanism 60 is provided to interact with the adjustment mechanism 37 and to automatically change the self-clearing material sensing apparatus 10 from the read configuration to the clearance configuration, and from the clearance configuration back to the read configuration. As shown in FIGS. 2 and 3, the actuating mechanism 60 includes an actuating cylinder 62 having a piston rod 64 pivotally connected (at 68) to the end of the extender arm 42 and a return spring 66 which is also connected to the extender arm 42. In a preferred embodiment, the cylinder is air-actuated, although any commonly known cylinder could be used. Preferably, a three-way solenoid valve 70 having a timer (not shown) is connected between the air line 72 and the actuating cylinder 62.

In the read configuration, the solenoid valve 70 is closed to prevent air flow to the cylinder and the return spring 66 maintains the extender arm 42 in a position where the side edges 40 of the tapered member 32 are disposed against the vertical plate 50. The timer is preset to periodically open the solenoid valve 70 to allow the air flow into the cylinder 62. At this time, the piston rod 64 of the cylinder 62 is extended to move the extender arm 42 further into the interior of the grain flow area 18 so that the material sensing apparatus 10 is changed to the clearance configuration. After the extender arm 42 has been fully extended to release any grain clogged in the funnel, the solenoid valve 70 closes and releases the air in the cylinder. At this time, the return spring 66 retracts the extender arm 42 to return the material sensing apparatus 10 to the read configuration. As the material sensing apparatus 10 moves between the read and clearance configurations, it will be appreciated that the cross-sectional area of the grain flow conduit 18 remains substantially constant so that the grain flow through the conduit is not substantially affected by the configuration of the material sensing apparatus. It will be appreciated that other types of actuating mechanisms may be utilized to periodically extend and retract the extender arm 42 between the read and clearance configurations.

It is further noted that when the extender arm 42 is extended outward to the clearance configuration, the extender arm pivot connection 44 follows an arcuate path about the funnel pivot connections 34. Accordingly, both extender arm connections (44 and 68) must permit the extender arm 42 to pivot in the vertical plane and the slot 54 in the vertical plate must also permit this vertical displacement of the extender arm 42. In the preferred embodiment, therefore, the connections at both ends of the extender arm 42 are pivoted connections.

Figure 4:
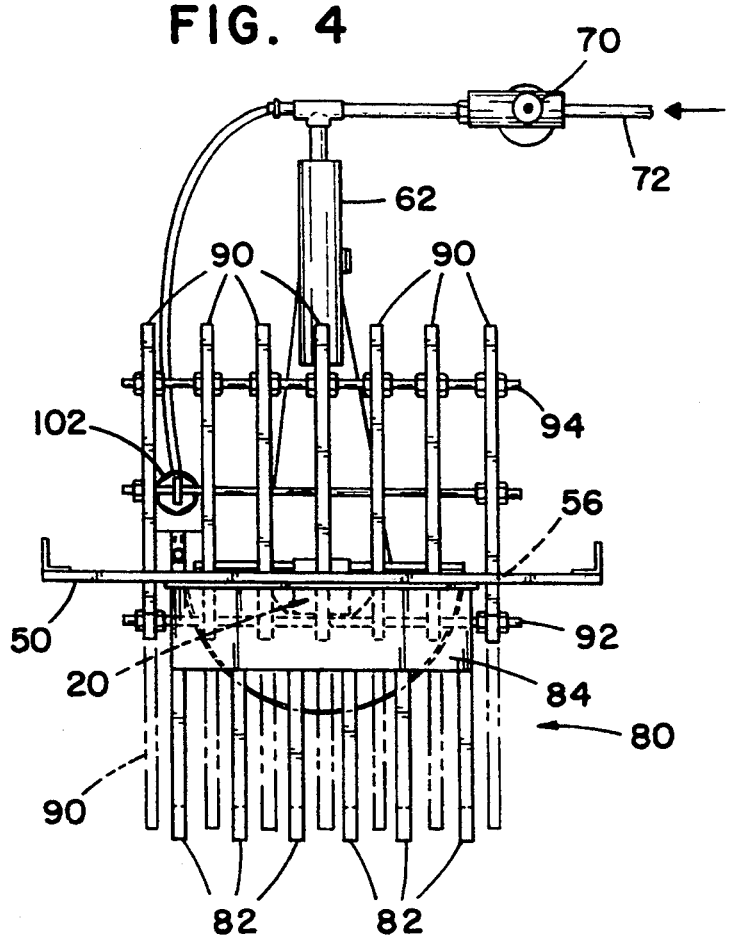
FIG. 4 is a top plan view of the self-clearing material sensing apparatus shown in FIG. 1.

In the preferred embodiment as illustrated in FIGS. 2 and 3, a scalper grate 80 is disclosed for preventing larger foreign objects from entering the funnel. The scalper grate is useful because the flowing grain may contain corn stalks or other larger foreign objects which could become lodged in the funnel and prevent the flow of grain through the funnel. The scalper grate 80 includes a plurality of slats 82 which are secured to a connector member 84. The connector member 84 is mounted to the vertical plate 50 at a position above the funnel inlet 36. As shown in FIG. 4, the slats 82 are spaced sufficiently apart to allow for the efficient flow of grain through the slats while still preventing larger foreign objects such as corn stalks, corn husks or the like from entering the funnel 30. Preferably, the scalper grate 80 is mounted to the vertical plate 50 such that the slats 82 are disposed at a downward angle. This allows foreign objects to deflect off the scalper grate 80 without blocking the upper inlet 36.

As an added precaution against potential clogging of the scalper grate 80 by foreign objects such as corn stalks and the like, the scalper grate 80 preferably includes clearing blades 90. In a preferred embodiment, these clearing blades 90 are pivotally mounted (at 92) within slots 56 in the vertical plate 50 for periodic insertion between the slats 82 of the scalper grate 80. When in a retracted position as shown in FIG. 2, the clearing blades 90 are disposed substantially outside the grain flow area proximate the funnel inlet 36 to permit the flow of grain through the scalper grate 80. When the scalper grate 80 is to be cleared, the clearing blades 90 pivot about the blade pivot connection 92 to a clearance position as shown in FIG. 3 and in phantom in FIG. 4. In this clearance position, the blades 90 are disposed between the slats 82 of the scalper grate 80, thus clearing any foreign object which may have been lodged between the slats of the scalper grate.

In a preferred embodiment, a second actuating mechanism 100 is provided to automatically rotate the clearing blades 90 between the retracted and clearance positions. This actuating mechanism 100 is similar to the first actuating mechanism 60 described above for the funnel extender arm 42. In particular, an actuating cylinder 102 is disposed beneath the clearing blades 90 with the cylinder piston rod 104 pivotally connected to the clearing blades through a blade-connecting bar 94, as illustrated in FIG. 4. Preferably, the cylinder 102 is air-actuated and connected to the same solenoid valve 70 and airline 72 as the extender arm actuating cylinder 62. It will be appreciated, however, that any commonly known cylinder may be used in the present invention and that the suitable actuating mechanisms may also be used within the present invention.

To clear the scalper grate 80, the timer (not shown) periodically opens the solenoid valve 70 and the piston rod 104 is extended upward to rotate the clearing blades 90 into the clearance position. After the scalper grate is cleared, the solenoid valve 70 closes and releases the air in the cylinder 102. An internal return spring (not shown) in the cylinder then retracts the piston rod 104 which rotates the clearing blades 90 back to the retracted position substantially outside the grain flow area 18. Additionally, the clearing blade actuating cylinder 102 is pivotally mounted to the vertical plate 50 through a hinge 106 to permit lateral movement of the cylinder as the piston rod 104 is extended upward.

In the preferred embodiment, the actuation of the extender arm 42 and clearing blades 90 occurs simultaneously since the cylinders are connected to a single air line 72. This reduces the number of actuating elements required for clearing the material sensing apparatus. It will be understood, however, that the extender arm 42 and clearing blades 90 could have separate actuating elements depending on the frequency required for clearing the funnel 30 and scalper grate 80.

It is to be understood that even though numerous characteristics and advantages of various embodiments of the present invention have been set forth in the foregoing description, together with details of the structure and function of various embodiments of the invention, this disclosure is illustrative only and changes may be made in detail, especially in matters of shape, size and arrangement of parts, within the principles of the present invention, to the full extent indicated by the broad general meaning of the terms in which the appended claims are expressed.

What is claimed is:

1. A self-clearing material sensing apparatus for sensing a physical parameter of a particulate material flowing through a conduit having a cross-sectional area, said self-clearing material sensing apparatus comprising:

a) a sensor device;

b) a funnel means located within the conduit for directing a consistent flow of the particulate material to an area proximate the sensor device, said funnel means having a read configuration and a clearance configuration, said funnel means further having an upper inlet and a lower outlet, the lower outlet including a narrowing below the upper inlet, the upper inlet having a first cross-sectional area and the narrowing having a second cross-sectional area, said first cross-sectional area being greater than said second cross-sectional area when said funnel means is in the read configuration, said funnel means further including narrowing adjustment means for increasing said second cross-sectional area when said funnel means is changed from the read configuration to the clearance configuration; and c) first actuation means for changing said funnel means from the read configuration to the clearance configuration and from the clearance configuration back to the read configuration such that the cross-sectional area of the conduit remains substantially constant; wherein said funnel means can channel the particulate material to the area proximate the sensor when said funnel means is in the read configuration and the particulate material can be efficiently released from the area proximate the sensor when said funnel means is changed from the read configuration to the clearance configuration.

2. A self-clearing material sensing apparatus according to claim 1 wherein said funnel means include a tapered member having a longitudinal axis and an opening along said axis and a vertical plate, said opening disposed adjacent the vertical plate when said funnel means is in the read configuration.

3. A self-clearing material sensing apparatus according to claim 2 wherein said narrowing adjustment means includes a pivotal connection securing the tapered member to the vertical plate adjacent the upper inlet and an extender arm pivotally attached to the tapered member below said pivotal connection such that the extension of the extender arm by said first actuation means in a direction away from the vertical plate rotates the tapered member about said pivotal connection to change said funnel means from the read configuration to the clearance configuration to substantially increase said second cross-sectional area of said narrowing.

4. A self-clearing material sensing apparatus according to claim 3 wherein said first actuation means includes an actuating cylinder, said actuating cylinder connected to said extender arm to selectively extend and retract said extender arm from the read configuration to the clearance configuration and from the clearance configuration to the read configuration, respectively.

5. A self-clearing material sensing apparatus according to claim 1 further comprising a scalper grate disposed above the upper inlet of said funnel means.

6. A self-clearing material sensing apparatus according to claim 5 wherein said scalper grate includes a plurality of slats wherein said slats are spaced sufficiently apart to allow the particulate material to efficiently flow into said upper inlet of said funnel means while preventing larger foreign objects from entering said upper inlet.

7. A self-clearing material sensing apparatus according to claim 6 further comprising means for clearing said scalper grate.

8. A self-clearing material sensing apparatus according to claim 7 wherein said means for clearing said scalper grate include a plurality of scalper clearing blades having a first retracted position and a second clearance position, said blades disposed substantially outside an area proximate said upper inlet when in said first retracted position and said blades disposed between said grate slats when in the second clearance position.

9. A self-clearing material sensing apparatus according to claim 8 further comprising second actuation means, said second actuation means including an actuating cylinder, said actuating cylinder connected to said scalper clearing blades to selectively extend and retract said scalper clearing blades from the first retracted position to the second clearance position and from the second clearance position to the first retracted position, respectively.

10. A self-clearing material sensing apparatus according to claim 1 wherein said sensor device is a moisture sensor for measuring the moisture content of the particulate material.

* * * * *